United States Patent
Johnson et al.

(10) Patent No.: US 10,105,172 B2
(45) Date of Patent: Oct. 23, 2018

(54) RADIOFREQUENCY AMPLIFIER IMPEDANCE OPTIMIZATION

(71) Applicant: COVIDIEN LP, Mansfield, MA (US)

(72) Inventors: Joshua H. Johnson, Arvada, CO (US); James A. Gilbert, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 607 days.

(21) Appl. No.: 14/445,745

(22) Filed: Jul. 29, 2014

(65) Prior Publication Data

US 2015/0105766 A1    Apr. 16, 2015

Related U.S. Application Data

(60) Provisional application No. 61/891,805, filed on Oct. 16, 2013.

(51) Int. Cl.
| | |
|---|---|
| *A61B 18/12* | (2006.01) |
| *H02M 7/5387* | (2007.01) |
| *H02M 7/48* | (2007.01) |
| *A61B 18/00* | (2006.01) |

(52) U.S. Cl.
CPC ............ *A61B 18/1206* (2013.01); *A61B 2018/00732* (2013.01); *A61B 2018/00875* (2013.01); *H02M 7/53871* (2013.01); *H02M 2007/4815* (2013.01); *Y02B 70/1441* (2013.01)

(58) Field of Classification Search
CPC ...... A61B 18/1206; A61B 2018/00875; A61B 2018/00732; H02M 2007/4815; H02M 7/53871; Y02B 70/1441
See application file for complete search history.

(56) References Cited

U.S. PATENT DOCUMENTS

| | | | |
|---|---|---|---|
| 4,429,694 A | 2/1984 | McGreevy | |
| 5,841,239 A | 11/1998 | Sullivan et al. | |
| 6,093,186 A | 7/2000 | Goble | |
| 6,582,427 B1* | 6/2003 | Goble | A61B 18/042 606/34 |
| D574,323 S | 8/2008 | Waaler | |
| 2002/0183804 A1 | 12/2002 | Malaney et al. | |
| 2004/0095100 A1 | 5/2004 | Thompson | |
| 2006/0043792 A1 | 3/2006 | Hjort et al. | |

(Continued)

FOREIGN PATENT DOCUMENTS

| | | |
|---|---|---|
| DE | 179607 C | 3/1905 |
| DE | 390937 C | 3/1924 |

(Continued)

OTHER PUBLICATIONS

European Examination Report dated Jun. 5, 2015. Issued in European Application No. 14185719.

(Continued)

*Primary Examiner* — Daniel Fowler
*Assistant Examiner* — Sean W Collins

(57) ABSTRACT

The present disclosure is directed to an electrosurgical generator including a resonant inverter having an H-bridge and a tank. The generator also includes a pulse width modulation (PWM) controller configured to output PWM timing signals to the H-bridge. A switch is configured to select a modality from among a plurality of modalities and the PWM controller adjusts a frequency of the PWM timing signals based on the selected modality.

8 Claims, 2 Drawing Sheets

(56) References Cited

U.S. PATENT DOCUMENTS

| | | | |
|---|---|---|---|
| 2007/0106349 A1* | 5/2007 | Karni | A61B 18/042 607/101 |
| 2007/0129716 A1 | 6/2007 | Daw et al. | |
| 2007/0173808 A1 | 7/2007 | Goble | |
| 2008/0114350 A1* | 5/2008 | Park | A61B 18/1206 606/34 |
| 2009/0036884 A1 | 2/2009 | Gregg et al. | |
| 2010/0114090 A1 | 5/2010 | Hosier | |
| 2010/0124035 A1 | 5/2010 | Bandholz et al. | |
| 2010/0137854 A1* | 6/2010 | Hosier | A61B 18/12 606/33 |
| 2011/0115562 A1* | 5/2011 | Gilbert | A61B 18/1206 330/262 |
| 2013/0023871 A1 | 1/2013 | Collins | |
| 2013/0267945 A1 | 10/2013 | Behnke, II et al. | |
| 2014/0104028 A1 | 4/2014 | Johnston | |
| 2014/0232463 A1 | 8/2014 | Gilbert | |
| 2015/0034406 A1 | 2/2015 | Hirose | |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2602517 A1 | 7/1976 |
| DE | 2504280 A1 | 8/1976 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 3904558 A1 | 8/1990 |
| DE | 3942998 A1 | 7/1991 |
| DE | 4206433 A1 | 9/1993 |
| DE | 4339049 A1 | 5/1995 |
| DE | 19506363 A1 | 8/1996 |
| DE | 19717411 A1 | 11/1998 |
| DE | 19848540 A1 | 5/2000 |
| DE | 10 2008058737 A1 | 4/2010 |
| EP | 0 246 350 A1 | 11/1987 |
| EP | 267403 A2 | 5/1988 |
| EP | 296777 A2 | 12/1988 |
| EP | 310431 A2 | 4/1989 |
| EP | 325456 A2 | 7/1989 |
| EP | 336742 A2 | 10/1989 |
| EP | 390937 A1 | 10/1990 |
| EP | 0 556 705 A1 | 8/1993 |
| EP | 608609 A2 | 8/1994 |
| EP | 0 836 868 A2 | 4/1998 |
| EP | 880220 A1 | 11/1998 |
| EP | 0 882 955 A1 | 12/1998 |
| EP | 1051948 A2 | 11/2000 |
| EP | 1064047 A1 | 1/2001 |
| EP | 1366724 A1 | 12/2003 |
| EP | 1776929 A1 | 4/2007 |
| EP | 2742888 A1 | 6/2014 |
| EP | 2829248 A1 | 1/2015 |
| FR | 1 275 415 A | 11/1961 |
| FR | 1 347 865 A | 1/1964 |
| FR | 2 313 708 A1 | 12/1976 |
| FR | 2364461 A1 | 4/1978 |
| FR | 2 502 935 A1 | 10/1982 |
| FR | 2 517 953 A1 | 6/1983 |
| FR | 2 573 301 A1 | 5/1986 |
| GB | 2 480 498 | 11/2011 |
| JP | 60-064765 | 4/1985 |
| JP | 63 005876 A | 1/1988 |
| JP | 2002-065690 A | 3/2002 |
| JP | 2005-185657 A | 7/2005 |
| JP | 2009-081183 A | 4/2009 |
| SU | 166452 | 11/1964 |
| SU | 727201 A2 | 4/1980 |
| WO | 9815317 A1 | 4/1998 |
| WO | 9947204 A1 | 9/1999 |
| WO | 02/11634 A1 | 2/2002 |
| WO | 02/45589 A2 | 6/2002 |
| WO | 03/090635 A1 | 11/2003 |
| WO | 06/050888 A1 | 5/2006 |
| WO | 08/053532 A1 | 5/2008 |
| WO | 2013-125010 A1 | 8/2013 |
| WO | 2014-062357 A1 | 4/2014 |

OTHER PUBLICATIONS

U.S. Appl. No. 14/297,812 dated Jun. 6, 2014, inventor: Wham.
U.S. Appl. No. 14/297,890 dated Jun. 6, 2014, inventor: Wham.
U.S. Appl. No. 14/320,762 dated Jul. 1, 2014, inventor: Gilbert.
U.S. Appl. No. 14/320,804 dated Jul. 1, 2014, inventor: Gilbert.
Wald et al., "Accidental Burns", JAMA, Aug. 16, 1971, vol. 217, No. 7, pp. 916-921.
Vallfors et al., "Automatically Controlled Bipolar Electrosoagulation—'COA-COMP'", Neurosurgical Review 7:2-3 (1984) pp. 187-190.
Sugita et al., "Bipolar Coagulator with Automatic Thermocontrol", J. Neurosurg., vol. 41, Dec. 1944, pp. 777-779.
Prutchi et al. "Design and Development of Medical Electronic Instrumentation", John Wiley & Sons, Inc. 2005.
Momozaki et al. "Electrical Breakdown Experiments with Application to Alkali Metal Thermal-to-Electric Converters", Energy conversion and Management; Elsevier Science Publishers, Oxford, GB; vol. 44, No. 6, Apr. 1, 2003 pp. 819-843.
Muller et al. "Extended Left Hemicolectomy Using the LigaSure Vessel Sealing System", Innovations That Work; Company Newsletter; Sep. 1999.
"Electrosurgical Unit Analyzer ESU-2400 Series User Manual" Apr. 1, 2002; Retrieved from Internet: <URL:http://www.bcgroupintl.com/ESU_2400/Updates/ESU-2400_UM_Rev04.pdf>, pp. 6, 11, 73.
Ogden Goertzel Alternative to the Fourier Transform: Jun. 1993 pp. 485-487, Electronics World; Reed Business Publishing, Sutton, Surrey, BG vol. 99, No. 9. 1687.
Hadley I C D et al., "Inexpensive Digital Thermometer for Measurements on Semiconductors", International Journal of Electronics; Taylor and Francis. Ltd.; London, GB; vol. 70, No. 6 Jun. 1, 1991; pp. 1155-1162.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Richard Wolf Medical Instruments Corp. Brochure, "Kleppinger Bipolar Forceps & Bipolar Generator", 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy", Journal Neurosurgery, 83; (1995) pp. 271-276.
Geddes et al., "The Measurement of Physiologic Events by Electrical Impedence", Am. J. MI, Jan. Mar. 1964, pp. 16-27.
Cosman et al., "Methods of Making Nervous System Lesions", In William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Benaron et al., "Optical Time-of-Flight and Absorbance Imaging of Biologic Media", Science, American Association for the Advancement of Science, Washington, DC, vol. 259, Mar. 5, 1993, pp. 1463-1466.

(56) References Cited

OTHER PUBLICATIONS

Cosman et al., "Radiofrequency Lesion Generation and Its Effect on Tissue Impedance", Applied Neurophysiology 51: (1988) pp. 230-242.
Zlatanovic M., "Sensors in Diffusion Plasma Processing" Microelectronics 1995; Proceedings 1995; 20th International Conference CE on Nis, Serbia Sep. 12-14, 1995; New York, NY vol. 2 pp. 565-570.
Ni W. et al. "A Signal Processing Method for the Coriolis Mass Flowmeter Based on a Normalized . . . ", Journal of Applied Sciences-Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297, Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone", Neurosurgery 15: (1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300", 1 p. Sep. 1998.
Valleylab Brochure "Valleylab Electroshield Monitoring System", 2 pp. Nov. 1995.
U.S. Appl. No. 10/406,690 dated Apr. 3, 2003 inventor: Behnke.
U.S. Appl. No. 10/573,713 dated Mar. 28, 2006 inventor: Wham.
U.S. Appl. No. 10/761,524 dated Jan. 21, 2004 inventor: Wham.
U.S. Appl. No. 11/242,458 dated Oct. 3, 2005 inventor: Becker.
U.S. Appl. No. 14/096,341 dated Dec. 4, 2013 inventor: Johnson.
U.S. Appl. No. 14/098,859 dated Dec. 6, 2013 inventor: Johnson.
U.S. Appl. No. 14/100,113 dated Dec. 9, 2013 inventor: Gilbert.
U.S. Appl. No. 14/147,294 dated Jan. 3, 2014 inventor: Gilbert.
U.S. Appl. No. 14/147,312 dated Jan. 3, 2014 inventor: Gilbert.
U.S. Appl. No. 14/168,296 dated Jan. 30, 2014, inventor: Mattmiller.
U.S. Appl. No. 14/174,551 dated Feb. 6, 2014 inventor: Johnson.
U.S. Appl. No. 14/174,607 dated Feb. 6, 2014 inventor: Friedrichs.
U.S. Appl. No. 14/179,724 dated Feb. 13, 2014 inventor: Johnson.
U.S. Appl. No. 14/180,965 dated Feb. 14, 2014 inventor: Larson.
U.S. Appl. No. 14/181,114 dated Feb. 14, 2014 inventor: Larson.
U.S. Appl. No. 14/182,797 dated Feb. 18, 2014 inventor: Wham.
U.S. Appl. No. 14/190,830 dated Feb. 26, 2014 inventor: Johnson.
U.S. Appl. No. 14/190,895 dated Feb. 26, 2014 inventor: Gilbert.
U.S. Appl. No. 14/255,051 dated Apr. 17, 2014 inventor: Coulson.
U.S. Appl. No. 14/262,219 dated Apr. 25, 2014, inventor: Gilbert.
U.S. Appl. No. 14/267,066 dated May 1, 2014, inventor: Friedrichs.
U.S. Appl. No. 14/268,187 dated May 2, 2014, inventor: Kerr.
U.S. Appl. No. 14/283,604 dated May 21, 2014, inventor: Behnke.
U.S. Appl. No. 14/297,771 dated Jun. 6, 2014, inventor: Wham.
European Search Report dated Oct. 28, 2015 issued in European Appln. No. 14185719.

* cited by examiner

US 10,105,172 B2

RADIOFREQUENCY AMPLIFIER IMPEDANCE OPTIMIZATION

CROSS REFERENCE TO RELATED APPLICATION

The present application claims the benefit of and priority to U.S. Provisional Application Ser. No. 61/891,805, filed on Oct. 16, 2013, the entire contents of which are incorporated herein by reference.

BACKGROUND

1. Technical Field

The present disclosure relates to radiofrequency amplifiers that use phase-shifted full bridge resonant inverters. Particularly, the present disclosure is directed to an electrosurgical system using a resonant inverter that achieves different tissue modalities with a single tank.

2. Background of the Related Art

Energy-based tissue treatment is well known in the art. Various types of energy (e.g., electrical, ultrasonic, microwave, cryogenic, thermal, laser, etc.) are applied to tissue to achieve a desired result. Electrosurgery involves application of high radio frequency electrical current to a surgical site to cut, ablate, coagulate or seal tissue. A source or active electrode delivers radio frequency energy from the electrosurgical generator to the tissue and a return electrode carries the current back to the generator. In monopolar electrosurgery, the source electrode is typically part of the surgical instrument held by the surgeon and applied to the tissue to be treated and the return electrode is placed remotely from the active electrode to carry the current back to the generator. In bipolar electrosurgery, one of the electrodes of the hand-held instrument functions as the active electrode and the other as the return electrode.

Electrosurgical generators may use a phase-shifted full bridge resonant inverter to generate the electrosurgical energy needed to perform the electrosurgical procedure. One example of a resonant inverter uses a LCLC tank topology driven by an H-bridge having two pairs of field effect transistors (FETs). Depending on the design of the LCLC tank, the resonant inverter is only capable of operating in one tissue modality. e.g., vessel sealing or cutting.

SUMMARY

This description may use the phrases "in an embodiment," "in embodiments," "in some embodiments," or "in other embodiments," which may each refer to one or more of the same or different embodiments in accordance with the present disclosure. For the purposes of this description, a phrase in the form "A/B" means A or B. For the purposes of the description, a phrase in the form "A and/or B" means "(A), (B), or (A and B)". For the purposes of this description, a phrase in the form "at least one of A, B, or C" means "(A), (B), (C), (A and B), (A and C), (B and C), or (A, B and C)".

As used herein, the term "generator" may refer to a device capable of providing energy. Such device may include a power source and an electrical circuit capable of modifying the energy outputted by the power source to output energy having a desired intensity, frequency, and/or waveform.

The systems described herein may also utilize one or more controllers to receive various information and transform the received information to generate an output. The controller may include any type of computing device, computational circuit, or any type of processor or processing circuit capable of executing a series of instructions that are stored in a memory. The controller may include multiple processors and/or multicore central processing units (CPUs) and may include any type of processor, such as a microprocessor, digital signal processor, microcontroller, or the like. The controller may also include a memory to store data and/or algorithms to perform a series of instructions.

Any of the herein described methods, programs, algorithms or codes may be converted to, or expressed in, a programming language or computer program. A "Programming Language" and "Computer Program" is any language used to specify instructions to a computer, and includes (but is not limited to) these languages and their derivatives: Assembler, Basic, Batch files, BCPL, C, C+, C++, Delphi, Fortran, Java, JavaScript, Machine code, operating system command languages, Pascal, Perl, PL1, scripting languages, Visual Basic, metalanguages which themselves specify programs, and all first, second, third, fourth, and fifth generation computer languages. Also included are database and other data schemas, and any other meta-languages. For the purposes of this definition, no distinction is made between languages which are interpreted, compiled, or use both compiled and interpreted approaches. For the purposes of this definition, no distinction is made between compiled and source versions of a program. Thus, reference to a program, where the programming language could exist in more than one state (such as source, compiled, object, or linked) is a reference to any and all such states. The definition also encompasses the actual instructions and the intent of those instructions.

Any of the herein described methods, programs, algorithms or codes may be contained on one or more machine-readable media or memory. The term "memory" may include a mechanism that provides (e.g., stores and/or transmits) information in a form readable by a machine such a processor, computer, or a digital processing device. For example, a memory may include a read only memory (ROM), random access memory (RAM), magnetic disk storage media, optical storage media, flash memory devices, or any other volatile or non-volatile memory storage device. Code or instructions contained thereon can be represented by carrier wave signals, infrared signals, digital signals, and by other like signals.

In an aspect of the present disclosure, an electrosurgical generator is provided. The electrosurgical generator includes a resonant inverter including an H-bridge and a tank and a pulse width modulation (PWM) controller that outputs PWM timing signals to the H-bridge. A switch selects a modality from among a plurality of modalities and the PWM controller adjusts a frequency of the PWM timing signals based on the selected modality.

The plurality of modalities includes at least a first modality and a second modality. If the first modality is selected, the PWM timing signals have a first switching frequency and if the second modality is selected, the PWM timing signals have a second switching frequency. The first switching frequency is different from the second switching frequency. The quality factor of the tank is greater than 1.

In another aspect of the present disclosure, an electrosurgical generator is provided. The electrosurgical generator has a resonant inverter including an H-bridge and a tank and a PWM controller configured to output PWM timing signals to the H-bridge. The electrosurgical generator also has a sensor circuit configured to measure at least one tissue property, wherein the PWM controller selects a modality based on the measured tissue property.

The sensor circuit measures an output voltage and an output current and the PWM controller determines a tissue impedance based on the output voltage and the output current. The PWM controller compares the tissue impedance with a threshold impedance. If the tissue impedance is less than the threshold impedance, the PWM controller selects a first modality, and if the tissue impedance is greater than the threshold impedance, the PWM controller selects a second modality. The quality factor of the tank is greater than 1.

In yet another aspect of the present disclosure, a method for controlling an electrosurgical generator including a resonant inverter having an H-bridge and a tank, a PWM controller, and a sensor circuit is provided. The method includes selecting a modality, setting a first switching frequency of the H-bridge based on the selected modality, and driving the H-bridge at the first switching frequency. A tissue impedance is determined based on at least one measurement provided by the sensor circuit and the tissue impedance is compared to a threshold impedance. The PWM controller drives the H-bridge at the first switching frequency if the tissue impedance is less than the threshold impedance and drives the H-bridge at a second frequency if the tissue impedance is greater than or equal to the threshold impedance. The frequency may also be selected for a certain modality and remain constant regardless of tissue impedance changes.

Selecting the modality may include outputting a test signal, calculating an initial tissue impedance, and selecting the modality based on the calculated tissue impedance.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1:
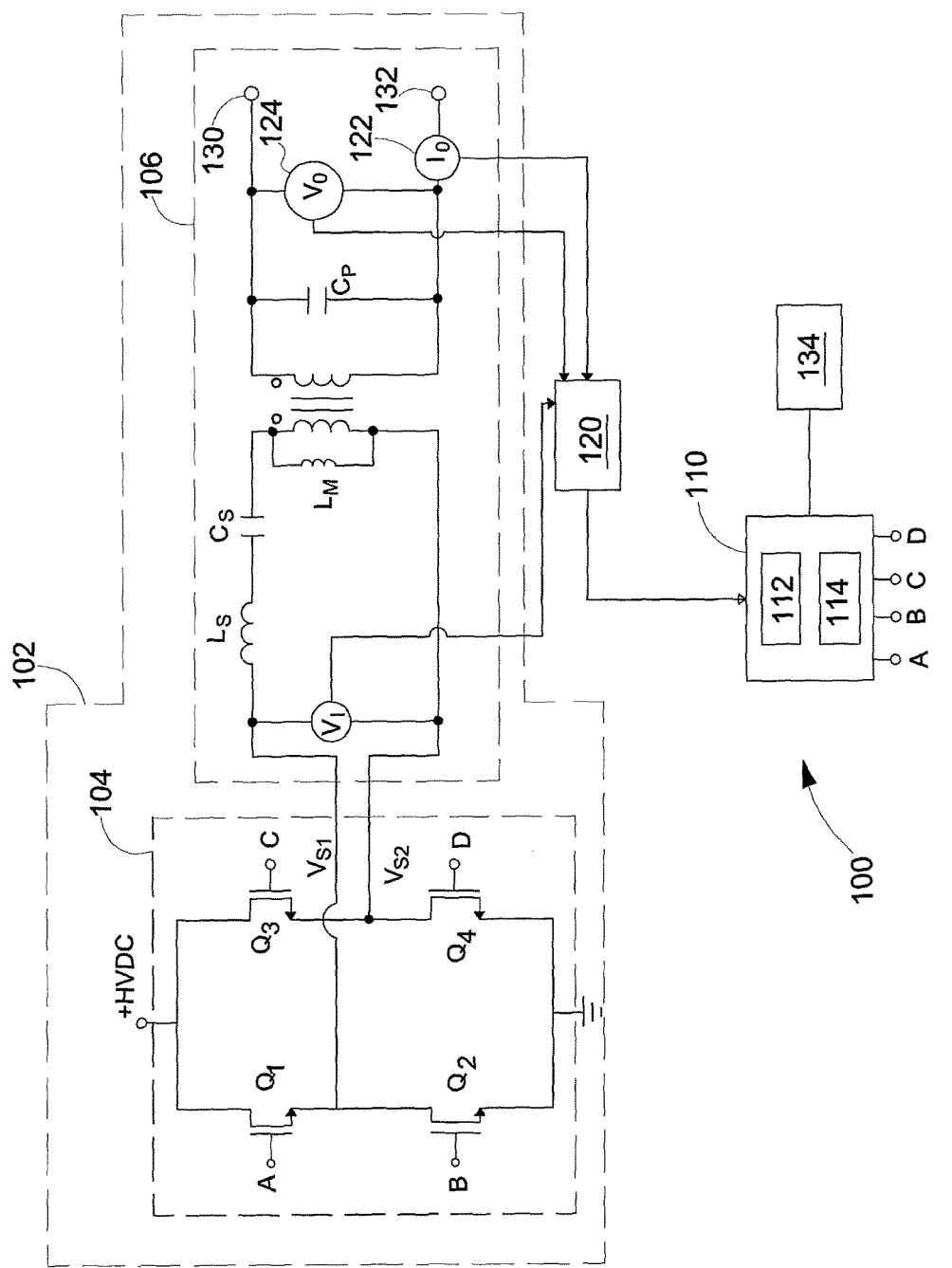
FIG. 1 is a schematic illustration of an electrosurgical generator in accordance with an embodiment of the present disclosure.

Particular embodiments of the present disclosure are described hereinbelow with reference to the accompanying drawings; however, it is to be understood that the disclosed embodiments are merely examples of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. Like reference numerals may refer to similar or identical elements throughout the description of the figures.

The present disclosure is directed to an electrosurgical generator that employs a phase-shifted full bridge resonant inverter having an LCLC tank topology and an H-bridge.

The generator adjusts the switching frequency of the H-bridge to achieve a different output impedance using a single LCLC tank. Allowing different impedances to be output from the electrosurgical generator allows the generator to operate in multiple modalities thereby reducing the cost of the generator.

Turning to FIG. 1, one example of an electrosurgical generator in accordance with an embodiment of the present disclosure is shown generally as 100. The generator 100 includes suitable input controls (e.g., buttons, activators, switches, touch screen, etc.) for controlling the generator 100. In addition, the generator 100 may include one or more display screens (not shown) for providing the user with variety of output information (e.g., intensity settings, treatment complete indicators, etc.). The controls allow the user to adjust power of the RF energy, waveform, as well as the level of maximum arc energy allowed which varies depending on desired tissue effects and other parameters to achieve the desired waveform suitable for a particular task (e.g., coagulating, tissue sealing, intensity setting, etc.). An instrument (not shown) that may be connected to the generator 100 may also include a plurality of input controls that may be redundant with certain input controls of the generator 100. Placing the input controls at the instrument allows for easier and faster modification of RF energy parameters during the surgical procedure without requiring interaction with the generator 100.

The generator 100 may include a plurality of connectors to accommodate various types of electrosurgical instruments. Further, the generator 100 may operate in monopolar or bipolar modes by including a switching mechanism (e.g., relays) to switch the supply of RF energy between the connectors.

The generator 100 includes a resonant inverter circuit 102, a pulse width modulation (PWM) controller 110, and a sensor circuit 120. The resonant inverter circuit 102 includes an H-bridge 104 having FETs Q1, Q2, Q3, and Q4 and an LCLC tank 106. The PWM controller 110 includes a processor 112 and a memory 114.

Figure 2:
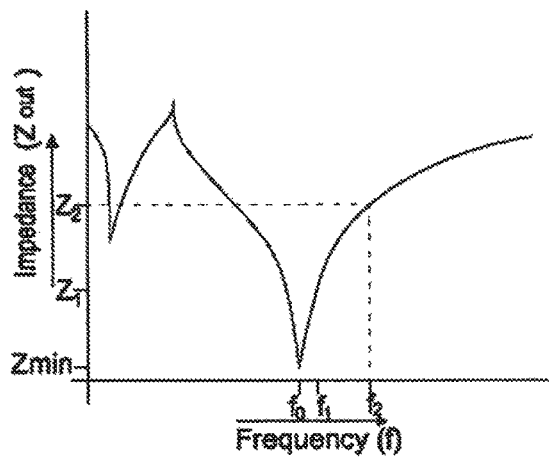
FIG. 2 is a graph depicting the relationship between the output impedance and frequency of the electrosurgical generator of FIG. 1.

In the resonant inverter circuit 102, the H-bridge 104 is supplied with a positive high voltage direct current (+HVDC). The series-parallel, or LCLC, converters of LCLC tank 106 are driven in a full-bridge configuration by the active FET switches Q1, Q2, Q3 and Q4. The PWM controller 110 supplies phase-shifted PWM timing signals to FET switches Q1, Q2, Q3 and Q4 as shown in FIG. 2. FETs Q1 and Q2 provide a voltage $V_{S1}$ to the LCLC tank 106 and FETs Q3 and Q4 provide a voltage $V_{S2}$ to the LCLC tank 106.

Components $L_S$, $C_S$, $L_M$ and $C_P$ are selected to provide resonant output amplitudes that are proportional to the phase-shifted PWM duty cycles times the power supply rail +HVDC and ground. The selection of $L_S$, $C_S$, $L_M$ and $C_P$ will be described in more detail below. The LCLC tank 106 outputs electrosurgical energy to an instrument (not shown) via active terminal 130. In particular, the active terminal 130 provides either continuous or pulsed sinusoidal waveforms of high RF energy. The active terminal 130 is configured to provide a plurality of waveforms having various duty cycles, peak voltages, crest factors, and other suitable parameters. Certain types of waveforms are suitable for specific electrosurgical modes. For instance, the active terminal 130 may provide a 100% duty cycle sinusoidal waveform in cut mode, which is best suited for ablating, fusing and dissecting tissue and a 1-25% duty cycle waveform in coagulation mode, which is best used for cauterizing tissue to stop bleeding.

A return terminal 132 is coupled to a return pad (not shown) for monopolar procedures. Alternatively, the return terminal 132 is electrically coupled to a return electrode (not shown) on an instrument.

The generator 100 may implement a closed and/or open loop control schemes which include the sensor circuit 120 having a plurality of sensors measuring a variety of tissue and energy properties (e.g., tissue impedance, tissue temperature, output current and/or voltage, etc.) and providing feedback to the PWM controller 110. A current sensor 122 can be disposed at either the active or return current path or both and provide an output current ($I_O$). A voltage sensor 124 can sense voltage at the terminals 130 and 132 and provide an output voltage ($V_O$). The output current ($I_O$) and the output voltage ($V_O$) are provided to the sensor circuit 120. Sensor circuit 120 may provide the output current and/or the output voltage to the PWM controller 110. The PWM controller 110 then transmits appropriate signals to FETs Q1, Q2, Q3, and Q4. The PWM controller 110 also receives input signals from the input controls of the generator 100 or the instrument. The PWM controller 110 utilizes the input signals to adjust power output by the generator 100 and/or performs other control functions thereon.

The sensor circuit 120 measures the input voltage ($V_I$) supplied to the LCLC tank 106, the output voltage ($V_O$) and output current ($I_O$) supplied by the active terminal 130 and the return terminal 132 in real time to characterize the electrosurgical process during a procedure. This allows for the measured electrical properties of the generator 100 and/or tissue being subjected to an electrosurgical process to be used as dynamic input control variables to achieve feedback control. The current and voltage values may also be used to derive other electrical parameters, such as power (P=V*I) and impedance (Z=V/I). The sensor circuit 120 may also measure properties of the current and voltage waveforms and determines the shape thereof.

The input voltage ($V_I$), the output voltage ($V_O$), and/or the output current ($I_O$) are provided to PWM controller 110 to implement a closed loop feedback scheme. As will be described in more detail below with respect to FIG. 3, the processor 112 of the PWM controller 110 may implement an algorithm stored in the memory 114 to adjust the frequency of the PWM timing signals provided to FETs Q1, Q2, Q3, and Q4.

Generator 100 also includes a switch 134 that allows a user to select one of a plurality of electrosurgical modalities for use during an electrosurgical procedure. The electrosurgical modalities may include, e.g., vessel sealing and e-cutting. The switch 134 may be any conventional switch having multiple poles that allows a user to select one of the electrosurgical modalities. Alternatively, in other embodiments, switch 134 may be a touch screen panel to allow a user to select one of the electrosurgical modalities. The operation of switch 134 is described below with reference to FIG. 2.

FIG. 2 illustrates a plot of the output impedance ($Z_{out}$) vs. frequency (f). As shown in the plot of FIG. 2, at frequency $f_0$, the output impedance of the LCLC tank 106 is at its lowest ($Z_{min}$). At frequency $f_1$, the output impedance $Z_1$ is increased exponentially with respect to the output impedance $Z_{min}$ at $f_0$. Frequency $f_1$ is kept above $f_0$ so that the H-bridge 104 is kept in zero-voltage switching. At frequency $f_2$, the output impedance $Z_2$ increases exponentially again with respect to the output impedance at In order to obtain relatively large changes in output impedance with small changes in frequency, the LCLC tank 106 is designed so that the gain of the impedance is close to resonance.

In the embodiments described herein, and in conjunction with FIG. 1, the LCLC tank 106 is designed to have a relatively large "Q" factor. The "Q" factor or quality factor of a resonant circuit is a measure of the quality of the circuit. The higher the "Q" factor, the narrower the bandwidth of the LCLC tank 106. Thus, in order to obtain relatively large changes in output impedance with small changes in frequency, the LCLC tank 106 is designed to have a high "Q" factor.

The "Q" factor of a series LC (inductor-capacitor) circuit is:

$$Q = \frac{1}{R}\sqrt{\frac{L}{C}} ; \qquad \text{(Equation 1)}$$

and the "Q" factor of a parallel LC circuit is:

$$Q = R\sqrt{\frac{C}{L}} , \qquad \text{(Equation 2)}$$

where R is the total resistance provided by the inductor(s) and the capacitor(s), L is the total inductance, and C is the total capacitance of the LC circuit. The components $L_S$, $C_S$, $L_M$ and $C_P$ of the LCLC tank 106 are selected so that the LCLC tank 106 has a high "Q" factor centered about the frequency $f_0$. For example, the "Q" factor may greater than 1.

In operation, when a user wants to perform a vessel sealing procedure, the user operates switch 134 to select the vessel sealing modality. Upon selecting the vessel sealing modality, the PWM controller 110 transmits appropriate signals to FETs Q1, Q2, Q3, and Q4 to operate at frequency $f_1$ so that the output impedance is $Z_1$. If the user wants to perform an e-cutting procedure, the user operates switch 134 to select frequency $f_2$ so that the output impedance is $Z_2$.

In another embodiment of the present disclosure, the generator 100 may automatically select a vessel sealing modality or an e-cutting modality. Memory 114 may store an algorithm, that when executed by processor 112, controls PWM controller 110 to switch between modalities. Switch 134 may be used to select the manual mode as described above or the automatic mode as will be described with reference to FIG. 3.

Figure 3:
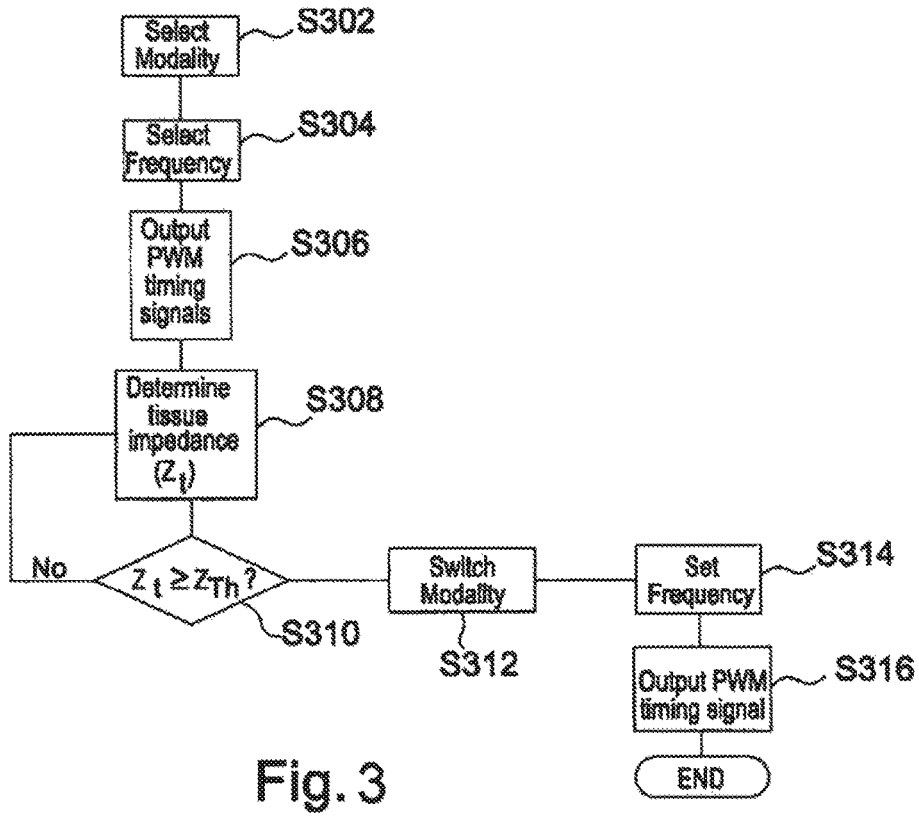
FIG. 3 is a flowchart depicting an algorithm executed by the electrosurgical generator of FIG. 1 in accordance with an embodiment of the present disclosure.

Turning to FIG. 3, which will be described in conjunction with FIG. 1, generator 100 selects a modality in step s302. The algorithm may initially set generator 100 in a vessel sealing modality or a user may select the vessel sealing modality. Upon selecting the modality in step s302, the processor 112 sets the switching frequency to $f_1$ in step s304 and the PWM controller 110 outputs the appropriate PWM timing signals to FETs Q1, Q2, Q3, and Q4 to drive H-bridge 104 at switching frequency $f_1$ (s306).

When tissue is heated, the impedance of the tissue is increased. Thus, the tissue impedance can be used to determine when a vessel sealing procedure is completed. Accordingly, in step s308, the tissue impedance ($Z_t$) is calculated. For example, current sensor 122 and voltage sensor 124 measure the output current ($I_O$) and output voltage ($V_O$) and provide the measurements to sensor circuit 120. Sensor circuit 120 may process the measurements provided by current sensor 122 and voltage sensor 124 and provide the measurements to PWM controller 110. Processor 112 of PWM controller 110 calculates a tissue impedance ($Z_t$)

based on the voltage and current measurements. In step s310, processor 112 compares the tissue impedance ($Z_t$) to a threshold impedance ($Z_{Th}$). If tissue impedance ($Z_t$) is less than threshold impedance ($Z_{Th}$), the algorithm returns to step s308 to determine the tissue impedance ($Z_t$).

If tissue impedance ($Z_t$) is greater than or equal to the threshold impedance ($Z_{Th}$), the algorithm proceeds to step s312 where the processor 112 selects the e-cutting modality. Upon selecting the e-cutting modality in step s312, the processor 112 sets the switching frequency to $f_2$ in step s314 and the PWM controller 110 outputs the appropriate PWM timing signals to FETs Q1, Q2, Q3, and Q4 to drive H-bridge 104 at switching frequency $f_2$ (s316).

In other embodiments, the initial modality selected in step s302 may be selected based on a measure tissue impedance. When the modality is based on a measured tissue impedance, the PWM controller 110 outputs a test signal to control FETs Q1, Q2, Q3, and Q4 for a predetermined amount of time. Sensor circuit 120 then receives output current ($I_O$) and output voltage ($V_O$) and calculates the tissue impedance. Based on the calculated tissue impedance, the PWM controller 110 selects the appropriate tissue modality.

Although the above-described embodiments highlight vessel sealing and e-cutting modalities, other modalities that may be used in electrosurgery can also be incorporated into the above-described embodiments.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figs. are presented only to demonstrate certain examples of the disclosure. Other elements, steps, methods and techniques that are insubstantially different from those described above and/or in the appended claims are also intended to be within the scope of the disclosure.

What is claimed is:

1. An electrosurgical generator comprising:
   a resonant inverter including a tank and exactly one H-bridge driving the tank, the H-bridge having exactly four switches;
   a pulse width modulation (PWM) controller configured to output PWM timing signals to the H-bridge, the PWM controller configured to set switching frequencies of the PWM timing signals; and
   a sensor circuit configured to measure at least one tissue property,
   wherein the PWM controller selects a modality based on the measured tissue property,
   wherein the tank is configured to provide a plurality of output impedances, the tank being configured such that increases in particular switching frequencies of the PWM timing signals cause exponential increases in output impedance of the tank, and
   wherein the PWM controller is configured to set the switching frequencies of the PWM timing signals to the particular switching frequencies that cause exponential increases in output impedance of the tank.

2. The electrosurgical generator of claim 1, wherein the sensor circuit measures an output voltage and an output current and the PWM controller determines a tissue impedance based on the output voltage and the output current.

3. The electrosurgical generator of claim 2, wherein the PWM controller compares the tissue impedance with a threshold impedance, wherein
   if the tissue impedance is less than the threshold impedance, the PWM controller selects a first modality, and
   if the tissue impedance is greater than the threshold impedance, the PWM controller selects a second modality.

4. The electrosurgical generator of claim 1, wherein the tank has a high quality factor.

5. The electrosurgical generator of claim 1, wherein the tank has a quality factor greater than 1.

6. The electrosurgical generator of claim 2, wherein the PWM controller is configured to set a first switching frequency for driving the H-bridge based on the selected modality.

7. The electrosurgical generator of claim 6, wherein the PWM controller is further configured to:
   compare the tissue impedance to a threshold impedance;
   drive the H-bridge at the first switching frequency if the tissue impedance is less than the threshold impedance; and
   drive the H-bridge at a second switching frequency if the tissue impedance is greater than the threshold impedance.

8. The electrosurgical generator of claim 2, wherein the PWM controller selecting a modality based on the measured tissue property includes the PWM controller selecting a modality based on the tissue impedance.

* * * * *